US 7,368,620 B2

(12) United States Patent
Zhou et al.

(10) Patent No.: US 7,368,620 B2
(45) Date of Patent: May 6, 2008

(54) TWO-STAGE AROMATICS ISOMERIZATION PROCESS

(75) Inventors: Lubo Zhou, Inverness, IL (US); Gregory F. Maher, Aurora, IL (US); James A. Johnson, Clarendon Hills, IL (US); John E. Bauer, LaGrange Park, IL (US)

(73) Assignee: UOP LLC, Des Plaines, IL (US)

( * ) Notice: Subject to any disclaimer, the term of this patent is extended or adjusted under 35 U.S.C. 154(b) by 205 days.

(21) Appl. No.: 11/171,964

(22) Filed: Jun. 30, 2005

(65) Prior Publication Data

US 2007/0004947 A1 Jan. 4, 2007

(51) Int. Cl.
    *C07C 5/27* (2006.01)
(52) U.S. Cl. .................. 585/319; 585/480; 585/481; 585/482
(58) Field of Classification Search ............... 585/319, 585/480, 481, 482
    See application file for complete search history.

(56) References Cited

U.S. PATENT DOCUMENTS

| | | | |
|---|---|---|---|
| 3,201,491 A | 8/1965 | Stine et al. | 260/676 |
| 3,626,020 A | 12/1971 | Neuzil | 260/674 SA |
| 3,696,107 A | 10/1972 | Neuzil | 260/674 SA |
| 3,856,872 A | 12/1974 | Morrison | 260/668 A |
| 3,923,639 A | 12/1975 | Ciric | 208/111 |
| 4,039,599 A | 8/1977 | Gewartowski | 260/668 A |
| 4,184,943 A | 1/1980 | Anderson | 208/310 R |
| 4,283,583 A | 8/1981 | Velenyi et al. | 585/467 |
| 4,381,419 A | 4/1983 | Wylie | 585/828 |
| 4,402,832 A | 9/1983 | Gerhold | 210/659 |
| 4,452,769 A | 6/1984 | Chu et al. | 423/329 |
| 4,482,774 A | 11/1984 | Koetsier | 585/481 |
| 4,758,419 A | 7/1988 | Lok et al. | 423/306 |
| 4,861,740 A | 8/1989 | Sachtler et al. | 502/66 |
| 4,899,011 A | 2/1990 | Chu et al. | 585/481 |
| 4,954,325 A | 9/1990 | Rubin et al. | 423/328 |
| 4,957,891 A | 9/1990 | Sachtler et al. | 502/61 |
| 5,240,891 A | 8/1993 | Patton et al. | 502/66 |
| 6,222,086 B1 | 4/2001 | Sharma et al. | 585/481 |
| 6,376,730 B1 | 4/2002 | Jan et al. | 585/467 |
| 6,448,459 B1 | 9/2002 | Magne-Drisch et al. | 585/478 |
| 6,576,581 B1 | 6/2003 | Sharma et al. | 502/66 |
| 6,660,896 B1 | 12/2003 | Buchanan et al. | 585/481 |
| 6,797,849 B2 | 9/2004 | McMinn et al. | 585/319 |
| 2005/0143614 A1 | 6/2005 | Leon-Escamilla et al. | 585/481 |
| 2005/0143615 A1 | 6/2005 | Bogdan et al. | 585/481 |

*Primary Examiner*—Thuan Dinh Dang
(74) *Attorney, Agent, or Firm*—Mary Ann Maas

(57) ABSTRACT

This invention is drawn to a process for isomerizing a non-equilibrium mixture of alkylaromatics in two sequential zones, the first zone operating in the absence of hydrogen using a platinum-free catalyst and the second zone using a catalyst comprising a molecular sieve and a platinum-group metal component to obtain improved yield of para-xylene from the mixture relative to prior art processes.

6 Claims, No Drawings

TWO-STAGE AROMATICS ISOMERIZATION PROCESS

FIELD OF THE INVENTION

This invention relates to catalytic hydrocarbon conversion, and more specifically to aromatics isomerization.

GENERAL BACKGROUND AND RELATED ART

The xylene isomers are important intermediates which find wide and varied application in chemical syntheses. Para-xylene is a feedstock for terephthalic acid which is used in the manufacture of synthetic textile fibers and resins. Meta-xylene is used in the manufacture of plasticizers, azo dyes, wood preservers, etc. Ortho-xylene is feedstock for phthalic anhydride production.

The proportions of xylene isomers obtained from catalytic reforming or other sources generally do not match demand proportions as chemical intermediates, and further comprise ethylbenzene which is difficult to separate or to convert. Para-xylene in particular is a major chemical intermediate with rapidly growing demand, but amounts to only 20-25% of a typical $C_8$-aromatics stream. Adjustment of isomer ratio to demand can be effected by combining xylene-isomer recovery, such as adsorption for para-xylene recovery, with isomerization to yield an additional quantity of the desired isomer. Isomerization converts a non-equilibrium mixture of the xylene isomers which is lean in the desired xylene isomer to a mixture approaching equilibrium concentrations.

Various catalysts and processes have been developed to effect xylene isomerization. In selecting appropriate technology, it is desirable to obtain a ratio of aromatic isomers as close to equilibrium as practical in order to maximize the para-xylene yield; however, a close approach to equilibrium is associated with a greater cyclic $C_8$ loss due to side reactions. The approach to equilibrium that is used is an optimized compromise between high $C_8$ cyclic loss at high conversion (i.e. very close approach to equilibrium) and high utility costs due to the large recycle rate of unconverted $C_8$ aromatics. Catalysts thus are evaluated on the basis of a favorable balance of activity, selectivity and stability.

Catalysts containing molecular sieves have become prominent for xylene isomerization in the past quarter-century or so. U.S. Pat. No. 3,856,872, for example, teaches xylene isomerization and ethylbenzene conversion with a catalyst containing ZSM-5, -12, or -21 zeolite. U.S. Pat. No. 4,899,011 teaches isomerization of $C_8$ aromatics using two zeolites, each of which is associated with a strong hydrogenation metal. U.S. Pat. No. 5,240,891 discloses a MgAPSO molecular sieve having a narrow ratio of framework magnesium and its use in xylene isomerization. U.S. Pat. No. 6,222,086 teaches the use of two zeolitic catalysts for the isomerization of a mixture of xylenes and ethylbenzene wherein the content of platinum-group metal in the second catalyst is no more than about 30% of that in the first catalyst. U.S. Pat. No. 6,448,459 discloses a process combination comprising recovery and isomerization of a first fraction of enriched ethylbenzene concentrate, recovery of para-xylene by adsorption from the second fraction from ethylbenzene enrichment, and isomerization of raffinate and desorbent from the para-xylene adsorption step. U.S. Pat. No. 6,660,896 teaches a process for isomerizing a feed containing ethylbenzene and a mixture of xylene isomers using first and second catalysts in the presence of hydrogen to produce a product having higher-than equilibrium para-xylene. Although these references teach individual elements of the present invention, none of the art suggests combination of the elements to obtain the critical features of the process of the present invention.

Catalysts for isomerization of $C_8$ aromatics ordinarily are classified by the manner of processing ethylbenzene associated with the xylene isomers. Ethylbenzene is not easily isomerized to xylenes, but it normally is converted in the isomerization unit because separation from the xylenes by superfractionation or adsorption is very expensive. A widely used approach is to dealkylate ethylbenzene to form principally benzene while isomerizing xylenes to a near-equilibrium mixture. An alternative approach is to react the ethylbenzene to form a xylene mixture via conversion to and reconversion from naphthenes in the presence of a solid acid catalyst with a hydrogenation-dehydrogenation function. The former approach commonly results in higher ethylbenzene conversion and more effective xylene isomerization, thus lowering the quantity of recycle in a loop of isomerization/para-xylene recovery and reducing concomitant processing costs, but the latter approach enhances xylene yield by forming xylenes from ethylbenzene. A catalyst system and process which combines the features of the approaches, i.e., achieves ethylbenzene isomerization to xylenes with high conversion of both ethylbenzene and xylenes, would effect significant improvements in xylene-production economics.

SUMMARY OF THE INVENTION

A principal object of the present invention is to provide a novel process using a combination of catalysts and systems tailored to specific reactions for isomerization of $C_8$-aromatic hydrocarbons to obtain improved yields of desired xylene isomers with low cyclic losses and recycle rate.

This invention is based on the discovery that a catalyst system comprising a combination of a liquid-phase process for the isomerization of xylenes in the absence of hydrogen and a vapor-phase process for converting ethylbenzene in $C_8$-aromatics yields a higher-than-equilibrium concentration of para-xylene.

A broad embodiment of the invention is a process for the isomerization of a non-equilibrium alkylaromatic feed mixture comprising one or more ethylaromatic hydrocarbons, comprising the sequential steps of: contacting the feed mixture in liquid phase in the substantial absence of hydrogen in a first isomerization zone with a first isomerization catalyst comprising from about 10 to 99 mass-% of at least one zeolitic aluminosilicate and an inorganic-oxide binder having the substantial absence of a platinum-group metal at first isomerization conditions to obtain an intermediate stream and contacting at least part of the intermediate stream in a second isomerization zone with a second isomerization catalyst comprising from about 0.1 to 2 mass-% of at least one platinum-group metal component, about 10 to 90 mass-% of at least one molecular sieve, and an inorganic-oxide binder at second isomerization conditions to obtain an isomerized product comprising a concentration of at least one alkylaromatic isomer that is higher than the equilibrium concentration at second isomerization conditions.

A more specific embodiment of the invention is a process for the isomerization of a non-equilibrium feed mixture comprising xylenes and ethylbenzene, comprising the sequential steps of contacting the feed mixture in liquid phase in the substantial absence of hydrogen in a first isomerization zone with a first isomerization catalyst comprising from about 10 to 99 mass-% of at least one zeolitic aluminosilicate and an inorganic-oxide binder and having the substantial absence of a platinum-group metal at first isomerization conditions to obtain an intermediate stream and contacting at least part of the intermediate stream in a second isomerization zone with a second isomerization catalyst comprising from about 0.1 to 2 mass-% of at least one platinum-group metal component, about 10 to 90 mass-% of at least one molecular sieve, and an inorganic-oxide binder at second isomerization conditions to obtain an isomerized product comprising a concentration of para-xylene that is higher than the equilibrium concentration at second isomerization conditions.

A yet more specific embodiment is a process for the isomerization of a non-equilibrium feed mixture comprising xylenes and ethylbenzene, comprising the sequential steps of contacting the feed mixture in liquid phase in the substantial absence of hydrogen in a first isomerization zone with a first isomerization catalyst comprising from about 10 to 99 mass-% of at least one zeolitic aluminosilicate and an inorganic-oxide binder and having the substantial absence of a platinum-group metal at first isomerization conditions to obtain an intermediate stream and contacting the entire intermediate stream in a second isomerization zone with a second isomerization catalyst comprising from about 0.1 to 2 mass-% of at least one platinum-group metal component, about 10 to 90 mass-% of at least one molecular sieve, and an inorganic-oxide binder at second isomerization conditions to obtain an isomerized product comprising a concentration of para-xylene that is higher than the equilibrium concentration at second isomerization conditions.

These as well as other objects and embodiments will become evident from the following detailed description of the invention.

DETAILED DESCRIPTION OF THE INVENTION

The non-equilibrium alkylaromatic feed mixture to aromatics isomerization comprises isomerizable alkylaromatic hydrocarbons of the general formula $C_6H_{(6-n)}R_n$, where n is an integer from 1 to 5 and R is $CH_3$, $C_2H_5$, $C_3H_7$, or $C_4H_9$, in any combination suitable for isomerization to obtain at least one more valuable alkylaromatic isomer in an isomerized product. The feed mixture comprises one or more ethylaromatic hydrocarbons containing at least one ethyl group, i.e., at least one R of at least one of the alkylaromatic hydrocarbons is $C_2H_5$. Suitable components of the feed mixture generally include, for example but without so limiting the invention, ethylbenzene, meta-xylene, ortho-xylene, para-xylene, ethyl-toluenes, trimethylbenzenes, diethyl-benzenes, triethylbenzenes, methylpropylbenzenes, ethylpropylbenzenes, diisopropylbenzenes, and mixtures thereof. The one or more ethylaromatic hydrocarbons are present in the feed mixture in a concentration of between about 2 and about 100 mass-%.

Isomerization of a non-equilibrium $C_8$-aromatic feed mixture comprising xylenes and ethylbenzene is a particularly preferred application of the present invention. Generally such mixture will have an ethylbenzene content in the approximate range of 1 to 50 wt-%, an ortho-xylene content in the approximate range of 0 to 35 wt-%, a meta-xylene content in the approximate range of 20 to 95 wt-% and a para-xylene content in the approximate range of 0 to 30 wt-%. By "non-equilibrium" is meant that at least one $C_8$-aromatic isomer is present in a concentration that differs substantially from the equilibrium concentration at second isomerization conditions. Usually the non-equilibrium mixture is prepared by removal of para-, ortho- and/or meta-xylene from a fresh $C_8$ aromatic mixture obtained from one or more aromatics-production or aromatics-conversion processes.

The alkylaromatic feed mixture may be derived from any of a variety of original sources, e.g., petroleum refining, thermal or catalytic cracking of hydrocarbons, coking of coal, or petrochemical conversions. Preferably the feed mixture utilized in the present invention is found in appropriate fractions from various petroleum-refinery streams, e.g., as individual components or as certain boiling-range fractions obtained by the selective fractionation and distillation of catalytically cracked or reformed hydrocarbons. The isomerizable aromatic hydrocarbons need not be concentrated; the process of this invention allows the isomerization of alkylaromatic-containing streams such as catalytic reformate with or without subsequent aromatics extraction to produce specified xylene isomers and particularly to produce para-xylene. A $C_8$-aromatics feed to the present process may contain nonaromatic hydrocarbons, i.e., naphthenes and paraffins, in an amount up to 30 wt-%. Preferably the isomerizable hydrocarbons consist essentially of aromatics, however, to ensure pure products from downstream recovery processes.

According to the process of the present invention, an alkylaromatic hydrocarbon feed mixture is contacted sequentially with two or more catalysts of the type hereinafter described respectively in first and second isomerization zones. Contacting may be effected in either zone using the catalyst system in a fixed-bed system, a moving-bed system, a fluidized-bed system, slurry system or ebullated-bed system or in a batch-type operation. In view of the danger of attrition loss of valuable catalysts and of the simpler operation, it is preferred to use a fixed-bed system in both zones.

In the preferred manner, the feed mixture is preheated by suitable heating means as known in the art to the desired reaction temperature and passes in liquid phase in the substantial absence of hydrogen into the first isomerization zone containing a fixed bed or beds of first isomerization catalyst. The term "substantial absence of hydrogen" means that no free hydrogen is added to the feed mixture and that any dissolved hydrogen from prior processing is substantially less than 0.05 moles/mole of feed, frequently less than 0.01 moles/mole, and possibly not detectable by usual analytical means. The first isomerization zone may comprise a single reactor or two or more separate reactors with suitable means therebetween to ensure that the desired isomerization temperature is maintained at the entrance to each reactor. The reactants may be contacted with the catalyst bed in upward-, downward-, or radial-flow fashion to obtain an intermediate stream which contains alkylaromatic isomers in a ratio which differs from that of the feed mixture. In the preferred processing of $C_8$-aromatics, the intermediate stream contains xylenes in proportions closer to equilibrium than in the feed mixture plus ethylbenzene in a proportion relating to that in the feed mixture.

The alkylaromatic feed mixture, preferably a non-equilibrium mixture of $C_8$ aromatics, contacts the first isomerization catalyst in liquid phase at suitable first isomerization conditions. Such conditions comprise temperature ranging from about 100° to about 500° C., and preferably from about 200° to 400° C. The pressure is sufficient to maintain the feed mixture in liquid phase, generally from about 500 kPa to 5 MPa absolute. The first isomerization zone contains a sufficient volume of catalyst to provide a liquid hourly space velocity with respect to the feed mixture of from about 0.5 to 50 $hr^{-1}$, and preferably 0.5 to 20 $hr^{-1}$.

At least part of the intermediate stream, and preferably the entire intermediate stream without a further processing step, is contacted in a second isomerization zone with a second isomerization catalyst. Preferably without passing through separation means, the intermediate stream is preheated by suitable heating means in the presence of a hydrogen-rich gas to the desired reaction temperature and then passed into the second isomerization zone containing a fixed bed or beds of the second isomerization catalyst. The second isomerization zone may comprise a single reactor or two or more separate reactors with suitable means therebetween to ensure that the desired isomerization temperature is maintained at the entrance to each reactor. The reactants may be contacted with the catalyst bed in upward-, downward-, or radial-flow fashion, and the reactants may be in liquid phase, a mixed liquid-vapor phase, or a vapor phase when contacted with the catalyst to obtain an isomerized product.

The intermediate stream, preferably a mixture of $C_8$ aromatics, contacts the second isomerization catalyst in the presence of hydrogen at suitable second isomerization conditions. Such conditions comprise a temperature ranging from about 200° to 600° C. or more, and preferably in the range of from about 300° to 500° C. The pressure generally is from about 100 kPa to 5 MPa absolute, preferably less than about 3 MPa. The second isomerization zone contains a sufficient volume of catalyst to provide a liquid hourly space velocity with respect to the intermediate stream of from about 0.5 to 50 $hr^{-1}$, and preferably 0.5 to 20 $hr^{-1}$. The intermediate stream optimally is reacted in admixture with hydrogen at a hydrogen/hydrocarbon mole ratio of about 0.5:1 to 25:1. Other inert diluents such as nitrogen, argon and light hydrocarbons may be present.

The isomerized product comprises a concentration of at least one alkylaromatic isomer that is higher than the equilibrium concentration at second isomerization conditions. The isomerized product preferably is a mixture of $C_8$ aromatics having a concentration of para-xylene that is higher than the equilibrium concentration at second isomerization conditions; preferably the concentration of para-xylene is at least 24.2 wt-%, often about 24.4 wt-% or more, and may be 25 wt-% or more. The $C_8$-aromatic ring loss relative to the feed mixture is usually less than about 3.5% and preferably less than about 3%.

The scheme employed to recover a particular isomer product from the isomerized product is not deemed to be critical to the instant invention, and any effective recovery scheme known in the art may be used. Typically, reactor effluent is condensed and the hydrogen and light-hydrocarbon components removed therefrom by flash separation. The condensed liquid product then is fractionated to remove light and/or heavy byproducts and obtain the isomerized product. In some instances, certain product species such as ortho-xylene may be recovered from the isomerized product by selective fractionation. The isomerized product from isomerization of $C_8$ aromatics usually is processed to selectively recover the para-xylene isomer, optionally by crystallization. Selective adsorption is preferred using crystalline aluminosilicates according to U.S. Pat. No. 3,201,491. Improvements and alternatives within the preferred adsorption recovery process are described in, for example, U.S. Pat. No. 3,626,020; U.S. Pat. No. 3,696,107; U.S. Pat. No. 4,039,599; U.S. Pat. No. 4,184,943; U.S. Pat. No. 4,381,419 and U.S. Pat. No. 4,402,832, incorporated herein by reference thereto.

In a separation/isomerization process combination relating to the processing of an ethylbenzene/xylene mixture, a fresh $C_8$-aromatic feed is combined with isomerized product comprising $C_8$ aromatics from the isomerization reaction zone and fed to a para-xylene separation zone; the para-xylene-depleted stream comprising a non-equilibrium mixture of $C_8$ aromatics is fed to the isomerization reaction zone, where the $C_8$-aromatic isomers are isomerized to near-equilibrium levels to obtain the isomerized product. In this process scheme non-recovered $C_8$-aromatic isomers preferably are recycled to extinction until they are either converted to para-xylene or lost due to side reactions.

The first isomerization catalyst favorably comprises a zeolitic aluminosilicate selected from those which have a $Si:Al_2$ ratio greater than about 10, preferably greater than 20, and a pore diameter of about 5 to 8 angstroms (Å). Specific examples of suitable zeolites are the MFI, MEL, EUO, FER, MFS, MTT, MTW, TON, MOR and FAU types of zeolites. Pentasil zeolites MFI and MTW are preferred.

A particularly favored MFI-type zeolite is gallium-MFI, with gallium as a component of the crystal structure. A preferred Ga-MFI has a $Si/Ga_2$ mole ratio of less than 500, and preferably less than 100; the aluminum content concomitantly is very low, with an $Si/Al_2$ mole ratio of greater than 500 and preferably greater than 1000.

The preparation of the preferred zeolites by crystallizing a mixture comprising an alumina and/or gallium source, a silica source and an alkali metal source is well known in the art. Conversion of an alkali-metal-form zeolite to the hydrogen form may be performed by treatment with an aqueous solution of a mineral acid. Alternatively, hydrogen ions can be incorporated into the pentasil zeolite by ion exchange with ammonium salts such as ammonium hydroxide or ammonium nitrate followed by calcination.

Microcrystalline materials favored as components of the second isomerization catalyst include one or more of BEA, MTW, FAU, MCM-22, UZM-8, MOR, FER, MFI, MEL, MTT, Omega, UZM-5, TON, EUO, OFF, NU-87 and MgAPSO-31.

A favored zeolitic molecular-sieve component of the second isomerization catalyst is MTW, also characterized as ZSM-12. A substantially mordenite-free MTW having a low silica-to-alumina ratio is particularly favored; such MTW zeolite is disclosed in US 2005/0143614 A1 and US 2005/0143615 A1, incorporated herein by reference thereto.

Alternatively, a favored crystalline non-zeolitic molecular sieve component of the second isomerization catalyst is one or more of the ATO framework types according to the ATLAS OF ZEOLITE STRUCTURE TYPES. The MgAPSO-31 molecular sieve of U.S. Pat. No. 4,758,419, having a crystallographic free diameter of 5.4 Å, is especially preferred. MgAPSO sieves have a framework structure of $MgO_2^{-2}$, $AlO_2^{-}$, $PO_2^{+}$, and $SiO_2$ tetrahedral units having an empirical chemical composition on an anhydrous basis expressed by the formula:

$$mR: (Mg_wAl_xP_ySi_z)O_2$$

wherein "R" represents at least one organic templating agent present in the intracrystalline pore system; "m" represents the molar amount of "R" present per mole of $(Mg_wAl_xP_ySi_z)O_2$ and has a value of zero to about 0.3; and "w", "x", "y" and "z" represent the mole fractions of elemental magnesium, aluminum, phosphorus and silicon, respectively, present as tetrahedral oxides. The mole fractions "w", "x", "y" and "z" are generally defined as being within the limiting compositional values or points as follows:

| | Mole Fraction | | |
|---|---|---|---|
| Point | x | y | (z + w) |
| A | 0.60 | 0.38 | 0.02 |
| B | 0.39 | 059 | 0.02 |
| C | 0.01 | 0.60 | 0.39 |

-continued

| | Mole Fraction | | |
|---|---|---|---|
| Point | x | y | (z + w) |
| D | 0.01 | 0.01 | 0.98 |
| E | 0.60 | 0.01 | 0.39 |

The MgAPSO-31 molecular sieve favorably may have a framework magnesium content of from about 0.003 to 0.035 mole fraction, consistent with the teachings of U.S. Pat. No. 5,240,891 which is incorporated herein by reference thereto.

The porous microcrystalline material of each of the first isomerization catalyst and the second isomerization catalyst preferably is composited with a binder for convenient formation of catalyst particles. The proportion of NZMS in the first catalyst is about 5 to 90 mass-%, preferably about 10 to 80 mass-%, the remainder other than metal and other components discussed herein being the binder component. The relative proportion of zeolite in the second catalyst may range from about 10 to about 99 mass-%, with about 20 to about 90 mass-% being preferred.

Usually catalyst particles of each of the first and second isomerization catalysts are homogeneous, with no concentration gradients of the catalyst components. However, it is within the scope of the invention that one or both of the catalysts is layered, for example with an outer layer of a bound zeolite bonded to a relatively inert core. Examples of layered catalysts can be found in U.S. Pat. No. 6,376,730; U.S. Pat. No. 4,482,774 and U.S. Pat. No. 4,283,583, incorporated herein by reference without so limiting the invention.

The binder should be porous, adsorptive support having a surface area of about 25 to about 500 $m^2/g$ which is relatively refractory to the conditions utilized in the hydrocarbon conversion process. It is intended to include within the scope of the present invention carrier materials which have traditionally been utilized in hydrocarbon conversion catalysts such as: (1) refractory inorganic oxides such as alumina, titania, zirconia, chromia, zinc oxide, magnesia, thoria, boria, silica-alumina, silica-magnesia, chromia-alumina, alumina-boria, silica-zirconia, etc.; (2) ceramics, porcelain, bauxite; (3) silica or silica gel, silicon carbide, clays and silicates including those synthetically prepared and naturally occurring, which may or may not be acid treated, for example attapulgite clay, diatomaceous earth, fuller's earth, kaolin, kieselguhr, etc.; (4) crystalline zeolitic aluminosilicates, either naturally occurring or synthetically prepared such as FAU, MEL, MFI, MOR, MTW (IUPAC Commission on Zeolite Nomenclature), in hydrogen form or in a form which has been exchanged with metal cations, (5) spinels such as $MgAl_2O_4$, $FeAl_2O_4$, $ZnAl_2O_4$, $CaAl_2O_4$, and other like compounds having the formula $MO-Al_2O_3$ where M is a metal having a valence of 2; and (6) combinations of materials from one or more of these groups.

A preferred refractory inorganic oxide for use in the catalyst composites of the present invention is alumina. Suitable alumina materials are the crystalline aluminas known as the gamma-, eta-, and theta-alumina, with gamma- or eta-alumina giving best results.

An alternative preferred binder is a form of amorphous silica. The preferred amorphous silica is a synthetic, white, amorphous silica (silicon dioxide) powder which is classed as wet-process, hydrated silica. This type of silica is produced by a chemical reaction in a water solution, from which it is precipitated as ultra-fine, spherical particles. It is preferred that the BET surface area of the silica is in the range from about 120 to 160 $m^2/g$. A low content of sulfate salts is desired, preferably less than 0.3 mass-%. It is especially preferred that the amorphous silica binder be nonacidic, e.g., that the pH of a 5% water suspension be neutral or basic (pH about 7 or above).

A preferred shape for each of the catalyst composites is an extrudate. The well-known extrusion method initially involves mixing of the non-zeolitic molecular sieve, either before or after adding metallic components, with the binder and a suitable peptizing agent to form a homogeneous dough or thick paste having the correct moisture content to allow for the formation of extrudates with acceptable integrity to withstand direct calcination. Extrudability is determined from an analysis of the moisture content of the dough, with a moisture content in the range of from 30 to 50 mass-% being preferred. The dough then is extruded through a die pierced with multiple holes and the spaghetti-shaped extrudate is cut to form particles in accordance with techniques well known in the art. A multitude of different extrudate shapes are possible, including, but not limited to, cylinders, cloverleaf, dumbbell and symmetrical and asymmetrical polylobates. It is also within the scope of this invention that the extrudates may be further shaped to any desired form, such as spheres, by marumerization or any other means known in the art.

A favored alternative shape of either of the composites is a sphere continuously manufactured by the well-known oil drop method. Preparation of alumina-bound spheres generally involves dropping a mixture of molecular sieve, alumina sol, and gelling agent into an oil bath maintained at elevated temperatures. Alternatively, gelation of a silica hydrosol may be effected using the oil-drop method. One method of gelling this mixture involves combining a gelling agent with the mixture and then dispersing the resultant combined mixture into an oil bath or tower which has been heated to elevated temperatures such that gelation occurs with the formation of spheroidal particles. The gelling agents which may be used in this process are hexamethylene tetraamine, urea or mixtures thereof. The gelling agents release ammonia at the elevated temperatures which sets or converts the hydrosol spheres into hydrogel spheres. The spheres are then continuously withdrawn from the oil bath and typically subjected to specific aging treatments in oil and an ammoniacal solution to further improve their physical characteristics.

The resulting composites then preferably are washed and dried at a relatively low temperature of about 50° to 200° C. and subjected to a calcination procedure at a temperature of about 450° to 700° C. for a period of about 1 to about 20 hours.

The first catalyst optionally is subjected to steaming to tailor its acid activity. The steaming may be effected at any stage of the zeolite treatment. Steaming conditions comprise a water concentration of about 5 to 100 vol-%, pressure of from about 100 kPa to 2 MPa, and temperature of between about 600° and 1200° C.; the steaming temperature preferably between about 650° and 1000° C., more preferably at least about 750° C. and optionally may be about 775° C. or higher. In some cases, temperatures of about 800° to 850° C. or more may be employed. The steaming should be carried out for a period of at least one hour, and periods of 6 to 48 hours are preferred. Alternatively or in addition to the steaming, the composite may be washed with one or more of a solution of ammonium nitrate, a mineral acid, and/or water. The washing may be effected at any stage of the preparation, and two or more stages of washing may be employed.

A platinum-group metal, including one or more of platinum, palladium, rhodium, ruthenium, osmium, and iridium, is an essential component of the second isomerization catalyst. The preferred platinum-group metal is platinum. The platinum-group metal generally comprises from about 0.1 to about 2 mass-% of the final catalyst, calculated on an elemental basis. The platinum-group metal component may exist within the final catalyst composite as a compound such as an oxide, sulfide, halide, oxysulfide, etc., or as an elemental metal or in combination with one or more other ingredients of the catalyst composite. It is believed that the best results are obtained when substantially all the platinum-group metal component exists in a reduced state.

A platinum-group metal component may be incorporated into the second isomerization-catalyst composite in any suitable manner. One method of preparing the catalyst involves the utilization of a water-soluble, decomposable compound of a platinum-group metal to impregnate the calcined sieve/binder composite. Alternatively, a platinum-group metal compound may be added at the time of compositing the sieve component and binder. Complexes of platinum-group metals which may be employed in impregnating solutions, co-extruded with the sieve and binder, or added by other known methods include chloroplatinic acid, chloropalladic acid, ammonium chloroplatinate, bromoplatinic acid, platinum trichloride, platinum tetrachloride hydrate, platinum dichlorocarbonyl dichloride, tetramine platinic chloride, dinitrodiaminoplatinum, sodium tetranitroplatinate (II), palladium chloride, palladium nitrate, palladium sulfate, diamminepalladium (II) hydroxide, tetramminepalladium (II) chloride, and the like. Preferably the platinum-group metal component is concentrated on the binder component of the catalyst by any method known in the art. One method of effecting this preferred metal distribution is by compositing the metal component with the binder prior to co-extruding the sieve and binder. The platinum-group metal component preferably is in higher concentration on the catalyst binder than on the SM-3 sieve component; more preferably about 60% or more, and most preferably at least about 80% of the platinum component is on the binder.

It is within the scope of the present invention that the second catalyst composite may contain other metal components known to modify the effect of the platinum-group metal component. Such metal modifiers may include rhenium, tin, germanium, lead, cobalt, nickel, indium, gallium, zinc, uranium, dysprosium, thallium, and mixtures thereof. Catalytically effective amounts of such metal modifiers may be incorporated into the catalyst by any means known in the art to effect a homogeneous or stratified distribution.

The catalysts of the present invention may contain a halogen component, comprising either fluorine, chlorine, bromine or iodine or mixtures thereof, with chlorine being preferred. Preferably, however, the catalyst contains no added halogen other than that associated with other catalyst components.

The second isomerization-catalyst composite is dried at a temperature of from about 1000 to about 320° C. for a period of from about 2 to about 24 or more hours and, usually, calcined at a temperature of from about 400° to about 650° C. in an air atmosphere for a period of from about 0.1 to about 10 hours until the metallic compounds present are converted substantially to the oxide form. If desired, the optional halogen component may be adjusted by including a halogen or halogen-containing compound in the air atmosphere.

The resultant calcined composite of the second isomerization catalyst optimally is subjected to a substantially water-free reduction step to insure a uniform and finely divided dispersion of the optional metallic components. The reduction optionally may be effected in the process equipment of the present invention. Substantially pure and dry hydrogen (i.e., less than 20 vol. ppm $H_2O$) preferably is used as the reducing agent in this step. The reducing agent contacts the catalyst at conditions, including a temperature of from about 200° to about 650° C. and for a period of from about 0.5 to about 10 hours, effective to reduce substantially all of the Group VIII metal component to the metallic state. In some cases the resulting reduced catalyst composite may also be beneficially subjected to presulfiding by a method known in the art to incorporate in the catalyst composite from about 0.05 to about 1.0 mass-% sulfur calculated on an elemental basis.

The foregoing description and following examples are presented only to illustrate certain specific embodiments of the invention, and should not be construed to limit the scope of the invention as set forth in the claims. There are many possible other variations, as those of ordinary skill in the art will recognize, within the spirit of the invention.

EXAMPLE I

Samples of catalysts were prepared for comparative pilot-plant testing. First, Catalyst A was prepared to represent a catalyst of the known art for isomerization of ethylbenzene to para-xylene.

Catalyst A containing MTW-type zeolite was prepared in accordance with U.S. Pat. No. 4,452,769 and US 2005/0143614 A1. To a solution of 0.2 mass-parts sodium hydroxide in 9 mass-parts distilled water were added 0.195 mass-parts aluminum hydroxide hydrate and the combined solution was stirred until dissolved. A second solution of 1.5 mass-parts of methyltriethylammonium chloride in 9 mass-parts distilled water was prepared and stirred until dissolved. Then, the two solutions were stirred together until homogenized. Next, 3 mass-parts of precipitated silica were added, stirred for 1 hour at room temperature and sealed in a Teflon-lined autoclave for 8 days at 150° C. Zeolite type MTW was recovered after cooling, filtering, and washing with distilled water. After drying, the recovered product was calcined at 550° C. to remove the template and ion-exchanged three times with NH4NO3 and dried to show an analysis: $0.9NH_4:Al_2O_3:41SiO_2:84H_2O$. The X-ray diffraction pattern was consistent with an MTW-structure zeolite.

To form Catalyst A, about 5 mass-% of the dry 100 mass-% MTW-zeolite was composited alumina to form spherical catalyst particles. The particles then were metal-impregnated using a solution of chloroplatinic acid. Upon completion of the impregnation, the catalyst was dried, oxidized, reduced, and sulfided to yield a catalyst containing about 0.3 mass-% platinum and 0.1 mass-% sulfur. The finished catalyst was labeled Catalyst A.

EXAMPLE II

Catalyst B was prepared using the MTW zeolite of Example I. About 80 mass-% of the dry zeolite was extruded with about 20 mass-% of alumina to form particles of Catalyst B. No metal was added to the catalyst.

EXAMPLE III

Catalyst C was prepared in accordance with the teachings of U.S. Pat. No. 4,957,891. A quantity of gallium-substituted pentasil zeolite having an X-ray diffraction pattern equivalent to that of ZSM-5 was prepared by adding a silica source, Ludox HS-40, to an aqueous solution containing an organic template, tetrapropylammonium bromide. The weight ratio of silica to template was about 4.9:1. A solution of sodium gallate was added to the silica and template mixture in an amount to give about 2 mass-% gallium based on the finished zeolite. The resultant mixture was autoclaved at about 125° C. for approximately 72 hours. The zeolite obtained was washed, filtered and dried to yield a gallium-substituted pentasil zeolite containing approximately 3 mass-% gallium.

A portion of the zeolite described above was mixed with alumina hydrosol, prepared by digesting metallic aluminum in hydrochloric acid, to yield a zeolite content in the finished catalyst equal to about 50 mass-%. To this mixture was added enough zirconium oxychloride sol, containing approximately 20 mass-% $ZrO_2$, such that the finished zeolite zirconia-alumina composite contained approximately 5 mass-% $ZrO_2$. Finally, a solution of hexamethylenetetramine was added as a gelling agent. The final mixture was dispersed as droplets into an oil bath at a temperature of about 95° C. The droplets remained in the oil bath until they formed hydrogel spheres. The spheres were removed from the oil bath and washed with an aqueous solution containing about 0.5 mass-% ammonia. The spheres were then air dried at 110° C. for about 12 hours and then calcined in air at a temperature of about 650° C. After calcination, the composite was washed with 0.5% $NH_3/H_2O$ solution at 95° C. and then oven-dried at 110° C. No platinum or sulfur was added to the catalyst.

EXAMPLE IV

Catalyst D was prepared in accordance with the teachings of U.S. Pat. No. 5,240,891. The reaction mixture was prepared by mixing the $Al_2O_3$ as pseudoboehmite (Versal 250) into the $H_3PO_4$ and water on a gradual basis and blending until a homogeneous mixture was observed. Magnesium acetate was dissolved in a portion of the water and then was added followed by addition of LUDOX-LS. The combined mixture was blended until a homogeneous mixture was observed. The organic templating agent (ethylbutylamine) and $AlPO_4$-31 seed were added to this mixture and blended until a homogeneous mixture was observed. Portions of the resulting mixture were placed in either lined (polytetrafluoroethylene) stainless steel pressure vessels for quiescent crystallization or an unlined stirred stainless steel pressure vessel and heated up to about 200° C. to effect crystallization at autogenous pressure. The products were removed from the reaction vessels and centrifuged to recover solids which were washed, dried and calcined at about 650° C. The resulting MgAPSO sieve, having a framework magnesium content of about 0.004 mole fraction, was extruded with alumina in a 50/50 mass ratio, impregnated to effect a platinum content of 0.3 mass-%, calcined, reduced and sulfided to yield Catalyst D.

EXAMPLE V

In an example of a single-catalyst system of the known art, Catalyst A was evaluated for ethylbenzene isomerization to para-xylene using a pilot plant flow reactor processing a non-equilibrium $C_8$ aromatic feed having the following approximate composition in wt-%:

| | |
|---|---|
| Toluene | 1.2 |
| $C_8$ Non-aromatics | 6.3 |
| Ethylbenzene | 13.9 |
| Para-xylene | 0.8 |
| Meta-xylene | 55.6 |
| Ortho-xylene | 22.2 |

The above feed was contacted with Catalyst A in the gas phase. Process conditions and the resulting performance measures are shown below:

| | |
|---|---|
| Temperature ° C. | 375 |
| Pressure, psig | 85 |
| WHSV, hr$^{-1}$ | 6 |
| H2:HC | 4 |
| p-xylene/xylenes, wt-% | 22.1 |
| EB conversion, wt-% | 35 |
| $C_8$ ring loss, % | 2.5 |

Note that the "$C_8$ ring loss" is in mol-% defined as "(1−($C_8$ naphthenes and aromatics in product)/($C_8$ naphthenes and aromatics in feed))*100", which represents material that has to be circulated to another unit in an aromatics complex. Such circulation is expensive and a low amount of $C_8$ ring loss is a preferred.

EXAMPLE VI

In an example showing performance of the present invention's first isomerization zone, Catalyst B was evaluated for meta-xylene and ortho-xylene isomerization to para-xylene using a pilot plant flow reactor processing a non-equilibrium $C_8$ aromatic feed having the same composition as in Example V.

This feed was contacted with Catalyst B in the liquid phase. Process conditions and the resulting performance measures are shown below:

| | |
|---|---|
| Temperature ° C. | 280 |
| Pressure, psig | 500 |
| WHSV, hr$^{-1}$ | 5 |
| p-xylene/xylenes, wt-% | 23.2 |
| EB conversion, wt-% | 3 |
| $C_8$ ring loss, % | 1.3 |

EXAMPLE VII

In another example showing performance of the present invention's first isomerization zone, Catalyst C was evaluated for meta-xylene and ortho-xylene isomerization to para-xylene using a pilot plant flow reactor processing a non-equilibrium $C_8$ aromatic feed having the same composition as in Example V.

This feed was contacted with Catalyst C in the liquid phase. Process conditions and the resulting performance measures are shown below:

| | |
|---|---|
| Temperature ° C. | 300 |
| Pressure, psig | 500 |
| WHSV, hr$^{-1}$ | 10 |
| p-xylene/xylenes, wt-% | 23.2 |
| EB conversion, wt-% | 3 |
| C$_8$ ring loss, % | 0.8 |

EXAMPLE VIII

In an example of the present invention's second isomerization zone, Catalyst D was evaluated for ethylbenzene isomerization to para-xylene using a pilot plant flow reactor processing a near-equilibrium C$_8$ aromatic feed having the same composition as the effluent from the reaction in Example VI. This feed was contacted with Catalyst D in the gas phase. Process conditions and the resulting performance measures are shown below:

| | |
|---|---|
| Temperature ° C. | 375 |
| Pressure, psig | 85 |
| WHSV, hr$^{-1}$ | 2 |
| p-xylene/xylenes, wt-% | 25.0 |
| EB conversion, wt-% | 31 |
| C$_8$ ring loss, % | 1.2 |

EXAMPLE IX

In an example of the present invention's second isomerization zone, Catalyst D was evaluated for ethylbenzene isomerization to para-xylene using a pilot plant flow reactor processing a near-equilibrium C$_8$ aromatic feed having the same composition as the effluent from the reaction in Example VII. This feed was contacted with Catalyst D in the gas phase. Process conditions and the resulting performance measures are shown below:

| | |
|---|---|
| Temperature ° C. | 375 |
| Pressure, psig | 85 |
| WHSV, hr$^{-1}$ | 2 |
| p-xylene/xylenes, wt-% | 25.0 |
| EB conversion, wt-% | 31 |
| C$_8$ ring loss, % | 1.2 |

EXAMPLE X

The combined results from the two-Isomerization zone system in comparison to the single-catalyst gas-phase system of the known art thus are as follows:

| Catalyst | B + D | C + D | A |
|---|---|---|---|
| p-xylene/xylenes, wt-% | 25.0 | 25.0 | 22.1 |
| EB conversion, wt-% | 34 | 34 | 35 |
| C$_8$ ring loss, % | 2.5 | 2.0 | 2.5 |

Equilibrium p-xylene/xylene ratio at 375° C. is 24.0 wt-%, so the two-zone example provides p-xylene at above equilibrium levels with C$_8$-aromatic ring loss equal to or less than in the example of the known art.

What is claimed is:

1. A process for the isomerization of a C$_8$-aromatic non-equilibrium feed mixture of xylenes and ethylbenzene comprising the sequential steps of:
    (a) contacting the feed mixture in the substantial absence of hydrogen in a first isomerization zone with a first isomerization catalyst consisting essentially of from about 10 to 99 mass-% of at least one zeolitic aluminosilicate selected from the group consisting of MTW, Ga-MFI, and a combination thereof, and an inorganic-oxide binder at first isomerization conditions to obtain an intermediate stream; and
    (b) contacting the entire intermediate stream in a second isomerization zone with a second isomerization catalyst comprising from about 0.1 to 2 mass-% of at least one platinum-group metal component, about 10 to 90 mass-% of at least one molecular sieve wherein the molecular sieve is a MgAPSO-31 molecular sieve having a framework magnesium content of from about 0.003 to about 0.035 mole fraction, and an inorganic-oxide binder at second isomerization conditions to obtain an isomerized product comprising a concentration of para-xylene that is higher than the equilibrium concentration at second isomerization conditions.

2. The process of claim 1 wherein the first isomeirization conditions comprise a temperature of from about 100° to about 500° C., a pressure of from about 500 kPa to 5 MPa and a liquid hourly space velocity of from about 0.5 to 50 hr$^{-1}$.

3. The process of claim 1 wherein the second isomerization conditions comprise a temperature of from about 200° to 600° C., a pressure of from about 100 kPa to 5 MPa, a liquid hourly space velocity of from about 0.5 to 50 hr$^1$, and a hydrogen/ hydrocarbon mole ratio of about 0.5:1 to 25:1.

4. The process of claim 1 wherein the C$_8$-aromatic ring loss relative to the feed mixture is less than about 3.5%.

5. The process of claim 4 wherein the C$_8$-aromatic ring loss relative to the feed mixture is less than about 3%.

6. The process of claim 1 further comprising processing a combination of the isomerized product and a fresh C$_8$-aromatic feed by selective adsorption to obtain high-purity para-xylene and the non-equilibrium feed mixture.

* * * * *